United States Patent [19]

Castelli et al.

[11] 4,378,432

[45] Mar. 29, 1983

[54] PROCESS FOR MANUFACTURING SWEETENED LIQUORS AND DERIVATIVES THEREOF FROM CELLULOSE-CONTAINING VEGETABLE SUBSTRATES

[75] Inventors: Michèle Castelli, Rueil Malmaison; Odile Chaudé, Sevres; Jean-Paul Vandecasteele, Fourqueux, all of France

[73] Assignee: Institut Francais du Petrole, Rueil-Malmaison, France

[21] Appl. No.: 305,767

[22] Filed: Sep. 25, 1981

[30] Foreign Application Priority Data

Sep. 25, 1980 [FR] France ................................ 80 20657

[51] Int. Cl.$^3$ ...................... C12P 19/02; C12P 19/14; C13K 1/02; A23K 1/00
[52] U.S. Cl. ....................................... 435/105; 435/99; 435/163; 435/165; 426/52; 426/53; 127/37
[58] Field of Search ................. 435/99, 163, 165, 105; 426/52, 53; 127/37

[56] References Cited

U.S. PATENT DOCUMENTS

| | | | |
|---|---|---|---|
| 3,642,580 | 2/1972 | Ghose | 435/105 |
| 4,058,411 | 11/1977 | Bellamy et al. | 127/37 |
| 4,201,596 | 5/1980 | Church et al. | 127/37 |
| 4,342,831 | 8/1982 | Faber et al. | 435/163 |

*Primary Examiner*—Lionel M. Shapiro
*Attorney, Agent, or Firm*—Millen & White

[57] ABSTRACT

Sweetened liquors are obtained from a cellulose-containing vegetable substrate by a process comprising two essential steps:
(a) treating the vegetable substrate with an aqueous solution of phosphoric acid alone or in admixture with sulfuric acid, and
(b) thereafter effecting enzymatic hydrolysis of the resultant treated substrate to recover additional reducing sugars.

9 Claims, No Drawings

PROCESS FOR MANUFACTURING SWEETENED LIQUORS AND DERIVATIVES THEREOF FROM CELLULOSE-CONTAINING VEGETABLE SUBSTRATES

BACKGROUND OF THE INVENTION

The acidic hydrolysis of vegetable substrates having a high cellulose and hemicellulose content in view, either of obtaining sugars as such, or of converting thereafter the sweetened liquors into various products such as ethyl alcohol, mixtures of acetone with butyl alcohol and isopropyl alcohol, yeasts for use as protein source, etc . . . has long been known.

However sufficient hydrolysis of the cellulosic substrates is only obtained when using high concentrations of acid and operating at high temperatures, which results in partial sugar destruction, high power requirements and use of expensive materials resistant to these severe conditions. For this reason other hydrolysis methods have more recently been sought, in particular methods operated with cellulase preparations (see, for example, U.S. Pat. No. 3,642,580 and European Pat. No. 0 011 767) which can be used at low temperature and have the advantage of avoiding sugar destruction.

However enzymatic hydrolysis is relatively slow and various treatments have been proposed to accelerate the conversion to sugars, such as mechanical treatments (U.S. Pat. No. 3,642,580) or alkaline treatments (French Pat. Nos. 2 359 206 and 2 327 315). The mechanical treatment has the disadvantage of a high power consumption while the alkaline treatment leads to soluble constituents liable to detrimentally affect the desired subsequent conversions and to pollute the residual liquors.

The object of the present invention is to provide a process for manufacturing sweetened liquors and resultant products from cellulose-containing vegetable substrates, which process does not suffer from the disadvantages of the known processes. This process substantially solves the problems linked to the use of the known severe acid treatment: sugar degradation, corrosion of apparatus, difficulty in disposing of acid solutions after use thereof. The new process also avoids the disadvantages of the conventional enzymatic treatment: insufficient yield, slow conversion.

SUMMARY OF THE INVENTION

The process of the invention comprises two essential steps, usually performed in the same reaction zone:
(a) in a first step, the vegetable substrate is treated with an aqueous solution of an acid, under hydrolysis conditions for cellulose-containing materials, and the treatment is discontinued when 10 to 45% of the potential reducing sugars have been formed. The acid is either phosphoric acid or a mixture of phosphoric acid with a minor amount of sulfuric acid;
(b) in a second step, an enzyme able to hydrolyse cellulose (cellulase) is added to the product of the first step and the resultant mixture is maintained at temperature and pH conditions allowing enzymatic hydrolysis of cellulose, said conditions being maintained for a sufficient time to form an additional amount of reducing sugars.

DETAILED DISCUSSION

By definition, a 100% yield of reducing sugars corresponds to the complete hydrolysis of cellulose and hemicellulose contained in the vegetable, which materials are titrated by the conventional anthrone method (HEBERT D., PHIPPS P. J. and STRANGE R. E. (1971); Methods in Microbiology 5B, 267).

It is possible, when using the two-step-process of the present invention, to obtain reducing sugars with yields of 50 to 80%, or more, of the theoretical value, the operation being effected under conditions which are mild, particularly advantageous as concerns energy and materials consumptions and which give practically no sugar decomposition products, in particular furfural.

The first step treatment is effected as follows:

The acid to be used is phosphoric acid alone or in admixture with sulfuric acid. Phosphoric acid, when compared with another acid ($H_2SO_4$, HCl) has the advantage of being less brutal and less corrosive. Phosphoric acid has also the advantage of supplying phosphorus to the medium, which element is necessary when the sweetened liquor must be subjected to further fermentation; it has also the advantage to allow an easy spreading of the final residual solutions which have a high content of nutritive elements. From the latter two points of view, and also depending on the nutritional requirements of the microorganisms employed in the fermentations carried out thereafter, it is sometimes advantageous to add to phosphoric acid small amounts of sulfuric acid which is an essential nutritive element, although in lower concentration, and which also allows the use of lower phosphoric acid concentrations for the treatment of vegetable substrates.

Finally, the use of phosphoric acid (alone or in admixture with sulfuric acid) has the essential advantage to avoid the formation of furfural by dehydration of sugars in the first step of the process, which furfural is detrimental to the subsequent enzymatic hydrolysis. The concentration of phosphoric acid (optionally in admixture with sulfuric acid) is so selected as to form, in the first step (thus during the pretreatment), less than 500 ppm of furfural, preferably less than 400 ppm and more particularly less than 300 ppm. The use of a strong acid, for example HCl or $H_2SO_4$, in the absence of phosphoric acid, leads to much higher furfural contents.

The amount of acid (phosphoric acid or phosphoric acid-sulfuric acid mixture) is between 2 and 10% by weight of the cellulose-containing material (cellulose-containing vegetable substrate) and preferably between 4 and 8%. The acid concentration in the aqueous hydrolysis solution used in the first step is preferably between 0.1 and 5% and more particularly between 0.25 and 2% by weight. When using a mixture of phosphoric acid with sulfuric acid, this mixture comprises, by weight, at most 30% of sulfuric acid is preferably less than 20% of sulfuric acid.

The conditions of the acid hydrolysis may be selected in a wide range, the essential being to limit the conversion to reducing sugars to 10–45% of the theoretical value. It is thus possible to operate, for example, at a temperature between 100° and 180° C. for 10 hours to 10 minutes. The preferred operating temperature is between 120° and 150° C. The conversion is the faster as the temperature is the higher; short reaction times are preferably associated with higher temperatures and conversely.

It is also advantageous, following the acid attack on the vegetable substrates and before the enzymatic hydrolysis, which is preferably effected at a pH between 3.5 and 7 and more preferably between 4 and 6, to neutralize the liquor with one or more bases which contain elements useful for the subsequent fermentation of the sugars as well as for the further use as fertilizers, for example, sodium hydroxide, potassium hydroxide, ammonia, sodium carbonate, potassium carbonate, ammonium carbonates or their mixtures.

From the vegetables usable as raw material in the present invention, the preferred ones are agriculture residues produced in large amounts, such as cereal straw or chaffs, linen anas, corn cobs or stalks, sugar-cane bagasse, residual stalks from oleaginous plants or even various vegetables insufficiently used and easily harvestable, such as copsewood, various residues from wood cutting or from saw-mills. These materials usually contain both cellulose and hemi-cellulose, for example, 35–40% of cellulose and 25–30% of hemi-celluloses in the case of straw.

Depending on the nature of the vegetable substrates employed, prior crushing of these vegetables can be effected, but this crushing must not necessarily be so thorough as when effecting the sole enzymatic treatment (crushing up to particles lower than 150μ or even 25μ is recommended in that case: U.S. Pat. No. 3,642,580); it is sufficient to effect a rough crushing or even a mere cutting, leading, for example, to particles of a size between 0.1 mm and 5 cm.

Depending on the nature of the substrates and the initial harvesting mode, it can be advantageous to effect the operations of rough crushing and acidic treatment simultaneously by using an appropriate device such as a cylinder-mixer, an extrusion device, a colloidal crusher, etc.

When the acid hydrolysis has given the desired conversion rate to reducing sugars, the medium is neutralized up to a pH of 3.5 to 7 and preferably 4 to 6, as shown above; the cellulase enzyme is added and the mixture is maintained at enzymatic hydrolysis conditions which are known as such.

Typical conditions are, for example, a temperature of 30° to 65° C., preferably 45° to 55° C., and enzymatic hydrolysis times of 6 to 120 h, preferably 20 to 50 h. Here also it is advantageous to associate the higher temperatures with the relatively shorter times and conversely.

The enzymes which are used are those having hydrolysis activity with respect to cellulose. It is also advantageous that they possess hydrolysis activity with respect to hemicelluloses. These enzymes are produced, in particular, by fungi of various species (Production of cellulolytic enzymes by fungi, T-M Enari and P. Markkanen, Advances in Biochemical Engineering, 5, 3-24 (1977)).

The invention will be better understood from the following examples:

EXAMPLE 1 (comparison)

No pretreatment is used in this example.

1 g of roughly cut wheat straw as particles of 0.1 of a few millimeters and whose water content is 7% is suspended in 25 ml of an aqueous acetate buffer of pH 4.8 to which is added a cellulase preparation of the trade (NOVO SP 122) in an amount providing a cellulase activity of 0.34 IU (international paper filter cellulase units) per millimeter of hydrolysis medium; the medium is maintained at 46° C. The amount of sugar in the solution is determined respectively at the 0 time and after 40 hours. This sugar amount is expressed as reducing sugars* and as glucose and pentoses*. The results obtained are given in the first column of Table I. It can be seen that 5.5 g/l of reducing sugars have been formed, which figure must be compared with the theoretical yield (potential reducing sugars) of 26 g/l.

*Miller G. L., Anal. Chemistry, 1959, 31,426.
**Bergmeyer, U. and Bernt, E. (1974) in "Methods in Enzymatic Analysis" H. U. Bergmeyer, ed. Verlag Chemie/Academic Press, Vol. 3, pp. 1205–1214.
***Ashwell, G. (1966) Methods in Enzymol, 8, 85–95.

(The results at the 0 time are those observed at the end of the pretreatment)

EXAMPLES 2 and 2 bis 1 g of the same roughly cut wheat straw is used, but it is previously treated with 8 ml of an aqueous phosphoric acid solution, the concentration of phosphoric acid corresponding to 4% by weight of the straw in example 2 and 1% in example 2 bis. The whole is autoclaved for 1 hour at 120° C. At this time, the furfural amount is negligible within the limits of experimental error (lower than 100 ppm). After cooling, the pH is adjusted (with sodium hydroxide), as well as the water and the enzyme contents, so as to be in the same conditions of enzymatic hydrolysis as in example 1. The temperature is maintained at 46° C. for 40 hours. The sugar content at the 0 time and after 40 hours respectively, with respect to the enzyme addition, as stated in Table I, show that whereas the initial sugar content is higher than in example 1, due to the prior acid hydrolysis, this content after 40 hours is considerably higher. The yields must be compared with the theoretical yield (identical for the examples 1 to 11 and 14 to 18) of 26 g/l.

EXAMPLE 3

The conditions are identical to those of example 2, except that the prior treatment is effected with 8 ml of an aqueous phosphoric acid solution corresponding to a 6% content with respect to the straw. The enzymatic hydrolysis of this example, as well as that of the examples 4 to 11, is identical to that of the examples 1 and 2. The results are given in Table I. The furfural amount at the end of the first step is negligible, being lower than 100 ppm.

EXAMPLE 4 and 4 bis

The conditions are the same as in example 2, except that 8 ml of aqueous phosphoric acid solution are used, the concentration of said acid being 8% by weight of the straw in example 4 and 9% in example 4 bis. The results of example 4 are given in Table I. In this example 4, the furfural content at the end of the first step is negligible, being lower than 100 ppm. The results of example 4 bis are substantially the same as in example 4; however the furfural content can be determined: it amounts to about 150 ppm within margins of experimental error.

EXAMPLE 5

The conditions are the same as in example 2, except that the pretreatment is effected with 4 ml of aqueous phosphoric acid solution, the latter acid amounting to 6% by weight of the straw. The results are given in Table I (the furfural amount at the end of the first step is lower than 100 ppm).

EXAMPLE 6

The conditions are the same as in example 2, except that 16 ml of aqueous phosphoric acid solution are used, the latter acid amounting to 6% b.w. of the straw. The results are given in Table I. The furfural amount at the end of the first step is lower than 100 ppm.

EXAMPLE 7

The conditions are the same as in example 5, except that the pretreatment is effected at 120° C. for 3 h. The results are given in Table I. The furfural amount at the end of the first step is about 150 ppm.

EXAMPLE 8

The conditions are those of example 5, except that the pretreatment is effected at 130° C. for 1 hour. The results are given in Table I. The furfural content at the end of the first step is about 130 ppm.

EXAMPLE 9

The conditions are the same as in example 5, except that the pretreatment is effected at 145° C. for 1 hour. The results are given in Table I. The furfural content at the end of the first step is about 250 ppm.

EXAMPLE 9 bis

Example 9 is repeated with a phosphoric acid concentration amounting to 10.1% by weight of the straw. 11.5 g/l of reducing sugars are obtained at the end of the pretreatment, i.e. at the zero time, the glucose and pentose amounts being respectively 3.7 and 7.9 (g/l) at the end of the pretreatment. The furfural amount is about 500 ppm.

EXAMPLE 10

The conditions are the same as in example 8, except that the pretreatment is effected with a mixture of phosphoric acid with sulfuric acid in the respective amounts of 2.5% and 0.5% b.w. of the straw, i.e. 17% by weight of sulfuric acid in the mixture of the two acids. The results are given in Table I. The furfural content at the end of the pretreatment is 200 ppm. When this example is repeated with sulfuric acid (3% of $SO_4H_2$) as the sole acid, there is obtained, at the end of the pretreatment, 12.5 g/l of reducing sugars, the glucose and pentose amounts being respectively 3.3 g/l and 7.6 g/l; however, the furfural amount, at the end of the pretreatment, is 1600 ppm.

EXAMPLE 11

The conditions are the same as in example 7, except that the pretreatment is effected with a mixture of phosphoric acid with sulfuric acid in the respective proportions of 2.5% and 0.5% b.w. of the straw. The results are given in Table I. The furfural content at the end of the pretreatment is about 220 ppm.

The following examples 12 to 18 relate more particularly to the selection of the operating conditions for the second step (b), adapted to a satisfactory use of the combined two steps (a) and (b).

EXAMPLE 12

The conditions are the same as in example 10, except that the volume of the final solution in which takes place the enzymatic hydrolysis is 10 ml instead of 25 ml, the enzymatic activity, expressed as international units, being then 0.85 IU per ml. The results, given in Table I, show that the final concentration of reducing sugars is substantially higher.

EXAMPLE 13

The conditions are those of example 12, except that the neutralization is effected with a mixture of 35 g/l KOH, 0.6 g/l NaOH and 6.5 g/l $NH_4OH$, instead of sodium hydroxide, the pH being always brought back to 4.8 before the enzymatic hydrolysis. The results given in Table I show that the nature of the neutralization medium for the acid does not modify substantially the final results.

EXAMPLE 14

The conditions are those of example 8, except that the enzymatic hydrolysis time is 80 hours instead of 40 hours. The results given in Table I show an increase of the sugar content.

EXAMPLE 15 and 16

The conditions are those of example 8, except that the enzymatic hydrolysis is effected at 50° C. and 40° C. respectively. The results are given in Table I.

EXAMPLE 17

The conditions are those of example 8, except that the enzymatic hydrolysis is effected with twice the cellulase concentration. The results are given in Table I.

EXAMPLE 18

The conditions are those of example 8, except that the neutralization of the medium, before enzymatic hydrolysis, is effected up to a pH of 5.5. The results are given in Table I.

The examples 19 to 21 relate to the use of the invention in various fermentations for producing proteins, fuels or fertilizers.

EXAMPLE 19

This example relates to the conversion of the resultant sugars to proteins. The conditions of example 13 are now applied to 1 kg of straw. After pretreatment and enzymatic hydrolysis with the cellulase solution, there are obtained 10 liters of solution containing 41 g/l of reducing sugars. The straw residue is filtered and washed with twice 1 liter of water; a solution containing 32 g/l of reducing sugars is thus obtained; the following oligo elements are added thereto up to the following concentrations: $MgCl_2$ (7.85 g/l), $FeSO_4$, 7 $H_2O$ (0.2 g/l), $CuSO_4$, 3 $H_2O$ (4.5 mg/l) and $ZnSO_4$, 7 $H_2O$ (53.7 mg/l).

The resultant solution is introduced into a 20 l aerated and stirred fermentation vessel, and a preculture of *Candida utilis* yeast is added.

The pH is maintained at 4.8 by periodical addition of 1 N ammonia and the temperature of the fermentation vessel is maintained at 34° C. After 15 h of aerobic fermentation, the ammonia supply is no longer necessary and it is found that the content of reducing sugars in the medium has reached 1.5 g/l. The cells are then collected by centrifugation and there is obtained a yeast residue of 700 g (wet weight). After drying, there is finally obtained 140 g of yeast which may be used as protein source, for example, for feeding animals.

EXAMPLE 20

This example, as well as example 21, relates to the production of a fuel mixture.

The pretreatment conditions of example 10 are applied to 1 kg of straw. Neutralization is effected with a mixture of KOH (35 g/l), NaOH (0.6 g/l) and ammonia (6.5 g/l), the pH being brought back to 4.8 before the enzymatic step. The enzymatic step is then effected and 19 g/l of reducing sugars are obtained after 40 hours. The same bases mixture is added to bring the pH to 6.5 and a solution containing 18.3 g/l of reducing sugars is obtained, to which solution the following oligo elements are added: $MgCl_2$ (2 g/l), $FeSO_4$, 7 $H_2O$ (0.05 g/l), $MnSO_4$, 5 $H_2O$ (0.02 g/l), $(NH_4)_6 Mo_7O_{24}$, 4 $H_2O$ (0.05 g/l), as well as a yeast extract (30 mg/l) and biotine (3 µg/l).

A preculture of *Clostridium acetobutylicum* bacteria strain is then prepared under known conditions, and used to seed under sterile conditions a 20 l fermentation vessel containing the above solution of reducing sugars. The culture is effected anaerobically under stirring at 37° C. for 70 hours. Thereafter, it is found that the reducing sugar content amounts to 2.3 g/l and that 4.0 g/l of a mixture comprising, by weight, 66% of butanol, 29% of acetone and 5% of ethanol have been obtained, which mixture is thereafter separated by distillation. The residual liquor is either used as such by spreading as fertilizer, or otherwise, before spreading and use as fertilizer, subjected to methanic fermentation.

EXAMPLE 21

The pretreatment of example 20 is repeated; neutralization is then effected with the KOH (35 g/l), NaOH (0.6 g/l) and ammonia (6.5 g/l) mixture up to a pH of 5.5; the oligo elements, the yeast extract and biotine of example 20 are also added. The enzymatic step is then effected as follows:

The solution obtained as above is introduced into a 20 l anaerobic fermentation vessel and the cellulase solution and the preculture of *Clostridium acetobutylicum* bacterium are added in the same proportions as in example 20, the temperature being maintained at 40° C. After 70 h, a residual content of reducing sugars of 0.9 g/l is obtained, as well as the production of 5 g/l of a mixture comprising, by weight, 66% of butanol, 29% of acetone and 5% of ethanol, which mixture is separated by distillation. The residual liquor is then either used as such by spreading as fertilizer, or otherwise, before spreading and use as fertilizer, subjected to methanic fermentation.

Examples 22 and 23 relate to the treatment of corn.

EXAMPLE 22 (comparison)

The conditions of example 1 are now applied to 1 g of corn residues previously dried (water content: 7.8%) and then crushed and sieved (holes of 3mm diameter). After 40 h, the reducing sugar content is 25.75 g/l, which figure is to be compared with the theoretical yield (potential reducing sugars) of 84 g/l. In the same conditions (thus after 40 h), the glucose and pentoses contents are respectively 12.3 and 7.7 g/l.

EXAMPLE 23

The conditions of example 3 are now applied to 1 g of the same corn residues as used in example 22. After 40 h, the reducing sugars content is 58 g/l, the glucose and pentoses contents being respectively 18.3 and 24.5 g/l.

TABLE 1

| PRODUCTS TITRATED BEFORE AND AFTER 40 h OF ENZYMATIC HYDROLYSIS | | EXAMPLE 1 | EXAMPLE 2 | EXAMPLE 3 | EXAMPLE 4 | EXAMPLE 5 | EXAMPLE 6 | EXAMPLE 7 | EXAMPLE 8 |
|---|---|---|---|---|---|---|---|---|---|
| Reducing sugars (g/liter) | 0 h | 0.35 | 2.5 | 3.5 | 5 | 3.9 | 3.6 | 9.7 | 9.5 |
| | 40 h | 5.5 | 12.6 | 14.5 | 15.8 | 13.8 | 15.1 | 19 | 18.5 |
| Glucose (g/liter) | 0 h | 0.09 | 0.66 | 0.91 | 1.21 | 0.93 | 0.95 | 0.60 | 0.81 |
| | 40 h | 2.5 | 4.7 | 5.7 | 6.25 | 5.3 | 5.9 | 6.2 | 5.5 |
| Pentoses (g/liter) | 0 h | 0.28 | 0.51 | 1.57 | 2.7 | 1.47 | 1.39 | 8.6 | 7.9 |
| | 40 h | 1.5 | 4.8 | 6.1 | 7.0 | 5.8 | 6.4 | 10.2 | 9.8 |

| PRODUCTS TITRATED BEFORE AND AFTER 40 h OF ENZYMATIC HYDROLYSIS | | EXAMPLE 9 | EXAMPLE 10 | EXAMPLE 11 | EXAMPLE 12 | EXAMPLE 13 | EXAMPLE 14 | EXAMPLE 15 | EXAMPLE 16 | EXAMPLE 17 | EXAMPLE 18 |
|---|---|---|---|---|---|---|---|---|---|---|---|
| Reducing sugars (g/liter) | 0 h | 10.1 | 9.9 | 8.7 | 21.3 | 22.1 | 9.3 | 9.8 | 9.5 | 9.2 | 9.6 |
| | 40 h | 19.8 | 19.5 | 18.3 | 41.1 | 41.5 | 20.1 (80 h) | 19.0 | 17.5 | 20.8 | 17.5 |
| Glucose (g/liter) | 0 h | 0.92 | 0.65 | 0.79 | 1.51 | 1.62 | 0.82 | 0.85 | 0.82 | 0.85 | 0.90 |
| | 40 h | 5.8 | 5.7 | 5.1 | 12.5 | 12.7 | 5.2 (80 h) | 4.9 | 4.1 | 6.7 | 3.9 |
| Pentoses (g/liter) | 0 h | 8.9 | 8.8 | 8.1 | 18.1 | 18.5 | 7.6 | 7.7 | 7.3 | 7.5 | 7.8 |
| | 40 h | 10.6 | 10.5 | 9.7 | 22.3 | 22.6 | 11.3 (80 h) | 10.2 | 9.2 | 11.7 | 9.1 |

What is claimed is:

1. A process for manufacturing a sweetened aqueous liquor from a cellulose-containing vegetable substrate, comprising the essential steps of:
   (a) treating said vegetable substrate with an aqueous solution of an acid under hydrolysis conditions for the cellulose contained in said substrate, up to formation of 10 to 45% of the potential reducing sugars, said acid being phosphoric acid or a mixture of phosphoric acid with sulfuric acid, said mixture comprising not more than 30% by weight of sulfuric acid, the concentration of said acid being from 2 to 10% by weight with respect to the vegetable substrate, thereby forming reducing sugars in said aqueous solution, and
   (b) adding an enzyme able to hydrolyse cellulose to the resultant treated substrate from step (a) and maintaining temperature and pH conditions allowing enzymatic hydrolysis of cellulose for a sufficient time to form an additional amount of reducing sugars, thereby obtaining a sweetened aqueous liquor.

2. A process according to claim 1, wherein said acid is used in a proportion of 4 to 8% by weight of the cellulose-containing vegetable substrate and wherein said hydrolysis conditions comprise a temperature from 100° to 180° C.

3. A process according to claim 2, wherein said acid is phosphoric acid and said temperature is from 120° to 150° C.

4. A process according to claim 2, wherein said acid is a mixture of phosphoric acid with sulfuric acid and said temperature is from 120° to 150° C.

5. A process according to claim 2, wherein the hydrolysis conditions of step (a) are so selected as to form not more than 500 ppm of furfural in the product of said step (a).

6. A process according to claim 1, wherein, in the step (a), the aqueous solution has a concentration of said acid between 0.1 and 5% by weight.

7. A process according to claim 1, wherein the pH conditions allowing enzymatic hydrolysis of cellulose comprise a pH of from 3.5 to 7 and this pH is obtained by addition, to the product of step (a), of at least one base selected from the group consisting of sodium hydroxide, potassium hydroxide, ammonia, sodium carbonate, potassium carbonate and ammonium carbonate.

8. A process according to claim 1, wherein the cellulose-containing vegetable substrate is straw.

9. A process according to claim 1, wherein the cellulose-containing vegetable substrate is corn.

* * * * *